United States Patent [19]

Hunter

[11] Patent Number: 5,067,509

[45] Date of Patent: Nov. 26, 1991

[54] GAS JET ACTUATOR USING COANDA EFFECT

[75] Inventor: Ian W. Hunter, Montreal, Canada

[73] Assignee: The Royal Institution for the Advancement of Learning (McGill University), Montreal, Canada

[21] Appl. No.: 546,742

[22] Filed: Jul. 2, 1990

[51] Int. Cl.[5] .................................................. F15C 1/08
[52] U.S. Cl. ........................................ 137/14; 137/830; 137/831
[58] Field of Search ................ 137/829, 830, 831, 832, 137/14

[56] References Cited

U.S. PATENT DOCUMENTS

| | | | |
|---|---|---|---|
| 3,053,276 | 9/1962 | Woodward | 137/829 |
| 3,289,687 | 12/1966 | Dunaway | 137/831 |
| 3,357,441 | 12/1967 | Adams | 137/831 |
| 3,797,527 | 3/1974 | Bain | 137/832 |

FOREIGN PATENT DOCUMENTS 1055919 1/1967 United Kingdom ................ 137/832

Primary Examiner—A. Michael Chambers
Attorney, Agent, or Firm—Burns, Doane, Swecker & Mathis

[57] ABSTRACT

A gas jet actuator device is described for imparting controlled vibrations to an object to which the device is connected. The device comprises a conduit defining an inlet section which is connectible to a source of gas pressure, and a fork section downstream of the inlet section to define two or more diverging outlet sections disposed at predetermined angles. A nozzle is provided in the conduit upstream of the fork section a predetermined distance therefrom. A switching device is provided to cause a pressurized fluid jet stream from said nozzle to be directed to selected ones of the outlet sections by the Coanda effect to impart a controlled vibration force to an object to which the device is attached.

15 Claims, 5 Drawing Sheets

GAS JET ACTUATOR USING COANDA EFFECT

BACKGROUND OF INVENTION

1. Field of Invention

The present invention relates to a gas jet actuator device operated by air pressure utilizing the Coanda effect to generate propulsing forces to impart controlled vibrations to an object to which the device is secured, and further to the method of vibrating an object using this device.

The gas jet actuator device of the present invention was developed particularly, but not exclusively, for testing the mechanical properties of a human or robotic arm. The gas jet actuator device constitutes an instrument when placed in a system for measuring the effects of an object when vibrations are imparted by the actuator device.

2. Description of Prior Art

Knowledge of the joint mechanical properties of the human arm during posture and movement is important for testing and inferring control strategies. Until recently, this knowledge has been limited to single-joint movements because instrumentation has not been available to apply appropriate spatial perturbations to the arm and to measure accurately the resulting displacements. The device of the present invention was developed to perturb arbitrary and natural multi-joint human arm movements, to measure accurately the force of perturbation and to allow the application of nonlinear stochastic system identification techniques to characterize the joint mechanical properties.

Previous arm studies have primarily used electric motors for perturbations. Advantages of electric motors are that power amplifiers and servo systems are readily available commercially, and that accurate position transducers are easily incorporated to measure rotor motion. Disadvantages are that they are bulky and heavy relative to their force or torque, and that they can only apply low-frequency perturbations because of the large rotor inertia and limitations in the power amplifiers. One consequence is that electric motors have been primarily applied to single-joint perturbation. In one known configuration, the a upper arm and forearm are strapped or cast into a single degree-of-freedom mechanical linkage, and the motor axis directly exerts torque on the coincident linkage and elbow joints. In another known configuration, the elbow point is fixed and a force is exerted directly on the wrist by an attached rod or cable running to the motor. Planar two-dimensional perturbations have been applied to the hand or wrist with two-link, parallel drive mechanisms driven by electric motors.

Perturbations have also been applied by hydraulic actuators, which offer advantages of much higher force or torque over electric motors for a given size. Depending on the servo-valve design, they may also provide a higher frequency output. They have been applied to the elbow and to the ankle.

Neither hydraulic actuators nor electric motors lend themselves readily towards a three-dimensional perturbation device. Although transmission elements such as rods or cables are conceivable, the dynamics of such elements are likely to confound the arm dynamics and to limit the perturbation bandwidth.

Recently, pneumatic thrusters have been devised as perturbation devices where compressed air is the power source and hydraulic spool valves control the air flow. Since gas jet nozzles can be mounted on a cuff attached to the wrist, they offer the possibility of multi-dimensional perturbations without significant constraints on arm movement. The tubing running to the cuff is light and flexible and does not impede movement, and the expelled air is of course not an environmental problem. These gas jet systems therefore represent a major advance in instrumentation because the experimentally imposed arm movement constraint is eliminated. A disadvantage of the spool valve design in these gas jets is spool mass and the resulting limitation on the system frequency bandwidth to about 20 Hz.

For any perturbation device designed to infer the human elbow's joint mechanical properties, a high frequency bandwidth is essential. There is reason to believe that these properties are nonlinear and time-varying and a high-frequency stochastic input is the best input to identify them. Even if a linear model is assumed, a high frequency is required to identify inertia reliably.

The gas jet actuator device of the present invention uses, as the primary control, a fluidic switching device, based on the Coanda effect. Such design greatly reduces the mass of mechanical moving parts and enhances the frequency bandwidth dramatically. This gas jet is intrinsically a bistable device that can generate arbitrary binary force sequences, such as pseudorandom binary sequences (PRBS), colored white noise, and Walsh functions. PRBS have been used as they are the most efficient implementation of a Gaussian white noise signal. An additional part of the system is the Optotrak (Registered Trademark—Northern Digital Inc., Waterloo, Ontario), a three-dimensional motion tracking system whose resolution is 0.05mm. The recent emergence of such high-accuracy measurement systems is essential for unrestrained arm movement studies in general and for our perturbation studies in particular.

SUMMARY OF INVENTION

It is a feature of the present invention to provide a gas jet actuator device for imparting controlled vibrations to an object. The device comprises conduit means defining an inlet section connectible to a source of fluid pressure. The conduit means has a fork section downstream of the inlet section to define two diverging outlet sections disposed at predetermined angles. A nozzle is provided in the conduit means upstream of the fork section a predetermined distance therefrom. Switching means is provided to cause a pressurized fluid jet stream from the nozzle to be directed to selected ones of the outlet sections by the Coanda effect to impart a controlled vibration force to an object to which the device is attached.

According to a still further broad aspect of the present invention there is provided a method of imparting a controllable vibration to a vibratable object. The method comprises attaching a gas jet actuator device to the object. The device has a conduit means defining an inlet section and a fork section downstream of the inlet section to define diverging outlet sections disposed at predetermined angles. A nozzle is provided in the conduit means upstream of the fork sections. Switching means is provided to cause a fluid jet stream from the nozzle to flow in an alternating sequence to the outlet sections. A flexible conduit is connected to the inlet section and to a remote pressure source. A predetermined fluid pressure is applied to the inlet section. The switching means is actuated to cause the jet stream to alternate between the outlet sections at frequencies within a predetermined frequency range of up to at least 100 Hz to impart vibrations to the vibratable object.

BRIEF DESCRIPTION OF DRAWINGS

A preferred embodiment of the present invention will now be described with reference to examples thereof as illustrated in the accompanying drawings in which.

DESCRIPTION OF PREFERRED EMBODIMENTS

Figure 1:
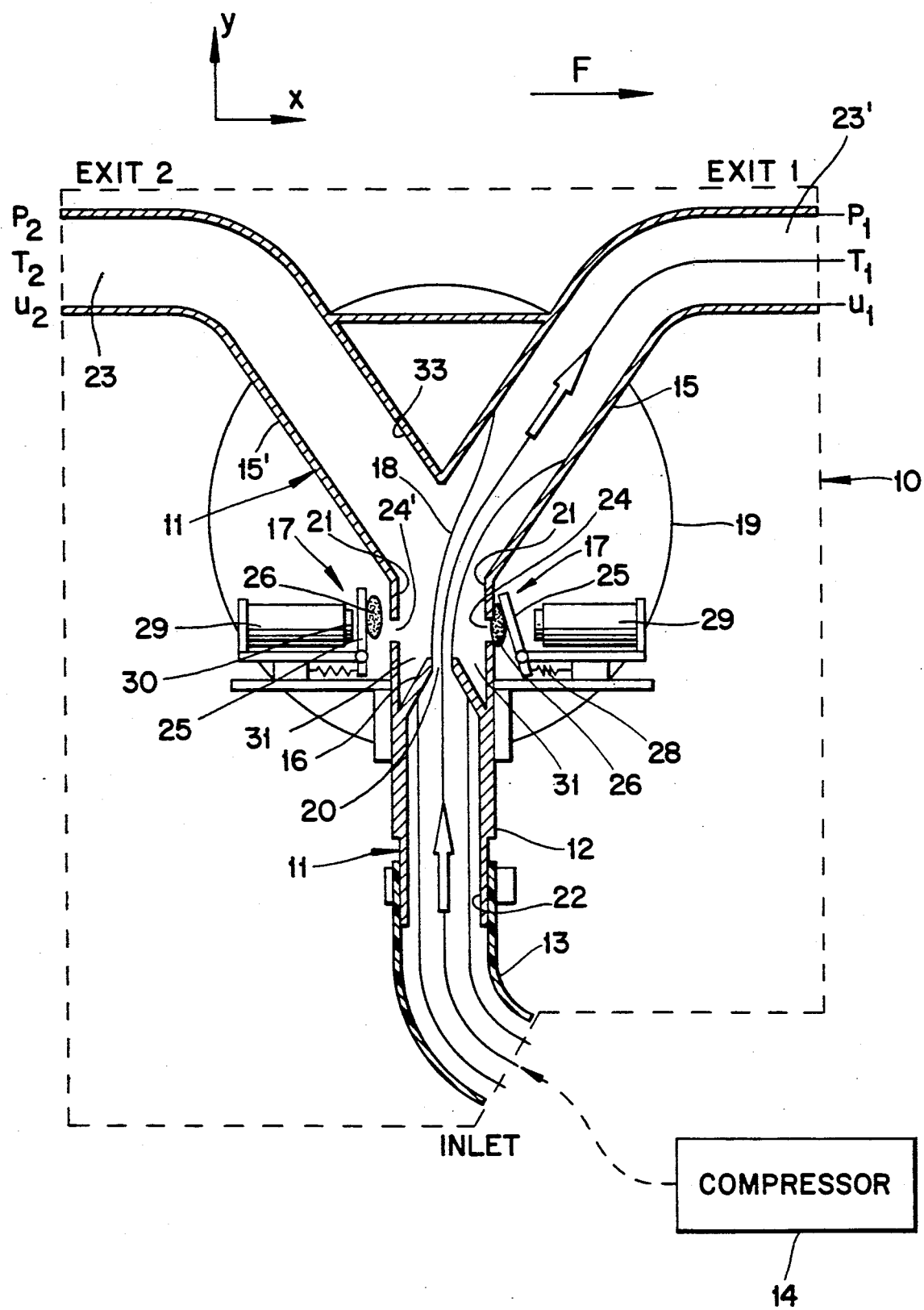
FIG. 1 is a schematic diagram of the gas jet actuator device.

The gas jet actuator device provides various advantages, such as (1) not change the properties of the system under study significantly, (2) perturb the system with enough power for high signal-to-noise ratio measurements, and (3) excite the system with adequate bandwidth for robust system identification. These specifications require some prior knowledge of the system and of the displacement-measuring apparatus capability. Here, we will discuss the human elbow joint as the system under study, even though the gas jet system design is not restricted to the forearm only.

Displacements are measured by the Optotrak, which uses three cameras to triangulate active markers (infrared light-emitting diodes (IREDs)) attached to the moving segment. Each camera contains a 2048 element linear CCD array and a cylindrical lens, which colimates the IRED beams. Due to a Gaussian spread of the light envelope, processes of thresholding and subpixel localization result in a dynamic range of $10^5:1$. The cameras are embedded in a solid aluminum block, and are automatically calibrated by accompanying software. The resolution is 0.05mm in a 0.25 m$^3$ viewing volume, and the highest sampling rate is 250 Hz for one IRED. If the perturbed motion has an RMS value of 0.2mm, the signal to noise ratio may be loosely calculated as SN=0.2/0.05=4 Therefore, a minimum 0.2mm perturbation is required at the highest frequency. This requirement will be used to estimate the amplitude of the force.

The most ubiquitous perturbation model in human motor control research is the second-order linear model. For single-joint movement such as at the elbow, $$I\ddot{\theta}_p + B\dot{\theta}_p + K\theta_p = \tau_p \tag{1}$$

where $\tau_p$ is the perturbation force, $\theta_p$, $\dot{\theta}_p$, $\ddot{\theta}_p$ are the joint position, velocity, and acceleration, and the mechanical impedance parameters I, B, K are the limb inertia, the joint viscosity and the joint stiffness. The mechanical impedance parameters B and K are commonly regarded as changing quantities controlled by the central nervous system (CNS); Equation (1) represents a quasilinear model applicable only about a specific operating point, e.g., some mean muscle activation level. I is usually reasonably constant during single-joint movement.

This linear perturbation model will be used to specify the perturbation force $\tau_p$ in terms of its type, frequency bandwidth, and amplitude. With regard to input type, a white noise random signal is the best input to identify a linear system because it leads to a maximum likelihood estimate and is particularly robust to noise. A random signal prevents predictive tracking and subsequent modification of the system response, as might be possible with a sinusoidal input. A random input is also extremely efficient and allows a system to be identified in a brief amount of time; this feature is especially important for nonstationary systems such as the biological motor control apparatus. A true white noise signal cannot be realized because it requires infinite power, and so pseudorandom signals designed for specific bandwidth ranges are widely used. Among pseudorandom signals, the pseudorandom binary sequence (PRBS) has maximum power for minimum amplitude range. When more is known about a system, a non-white binary sequence may be designed to optimally identify the system. The gas jet actuator device of the present invention is a controllable bistable device which generates binary force sequences naturally.

The required frequency range can be determined from Equation (1) with a priori knowledge on the possible values of the parameters I,B,K. The transfer function is obtained via the Laplace transform:

$$\frac{\theta_p}{\tau_p} = \frac{1}{Is^2 + Bs + K} = \frac{1}{K} \frac{\omega_n^2}{s^2 + 2\xi\omega_n s + \omega_n^2}. \tag{2}$$

where $\omega_n = \sqrt{K/I}$ is the natural frequency and $\xi = B/2\sqrt{IK}$ is the damping parameter.

If the input signal contains only low frequencies (s→0), then $\theta_p/\tau_p \approx 1/K$ and only K is accurately identified.

If the input signal contains only high frequencies (s→∞), then $\theta_p/\tau_p \approx 1/I$ and only I is accurately identified.

If the input signal has sufficient frequency content around the system natural frequency (s→$\omega_n$), then $\theta_p/\tau_p \approx 1/(2K(1+\xi))$ and B can be accurately identified if K and I are known.

In general, the input signal should have a frequency content of at least twice $\omega_n$. Experiments have been performed on the human forearm with a sinusoidal force input, and it has been estimated that the natural frequency for the human elbow joint is as high as 25 Hz. Although the muscle afferents are known to respond to frequencies in excess of 100 Hz, the musculoskeletal system acts as a second-order, low-pass filter with a much lower corner frequency. Because of this the gas jet actuator device of the present invention has a frequency content up to 100 Hz.

The force amplitude is large enough to produce measurable deflection at the highest frequency. If the arm is initially at rest, then for a constant initial acceleration the force is:

$$F = \frac{I}{l^2}\left(\frac{2d}{t_r^2}\right) \tag{3}$$

where d=0.2mm is the smallest deflection reliably measured by the Optotrak (SNR=4) and $t_r$=0.01 s is the rise time (100 Hz). For a typical adult male, the distance from the elbow to wrist is 0.25 m, and the moment of inertia of the forearm and hand about the elbow is 0.06 Nms$^2$. The required perturbation force is then 4N and 100 Hz. Higher forces and frequencies may be impractical. Because the force depends on the square of time or frequency, a higher frequency requires considerably more force. Excessively high forces may not be suitable for a small perturbation analysis to derive a linearized characterization of the true nonlinear arm dynamics. Projecting ahead the requirements for perturbation at the shoulder joint, the added inertia of the forearm plus upper arm is roughly canceled by the increased lever arm through which the force acts.

Figure 3:
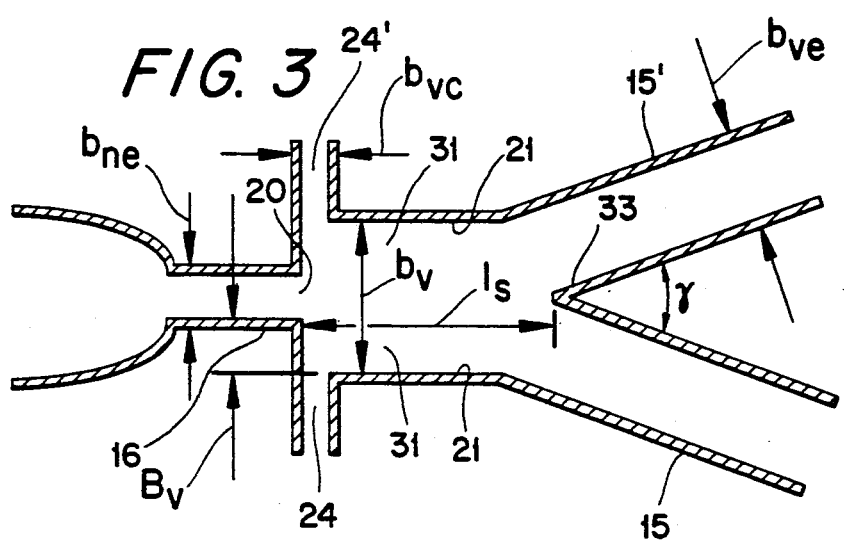
FIG. 3 is a schematic illustration showing the valve portion dimensions for the gas jet.

Referring now to FIG. 1, there is shown generally at 10 the gas jet actuator device of the present invention. It is comprised of a conduit means herein provided with a guide tube 11 which defines a straight inlet section 12 connectible to a flexible hose 13 leading to a remote pressure source, such as a compressor 14 to apply a predetermined fluid pressure to the inlet section 12. The guide tube also defines a fork section, herein shown as constituted by two diverging tubular outlet sections 15, 15' disposed at predetermined angles with respect to the inlet section 12. A nozzle 16 is disposed in the conduit 12 a predetermined distance from the fork section, as will be described later with reference to FIG. 3, wherein to eject therefrom a pressurized fluid jet stream in the direction of the fork section. Switching means 17 is associated with each of the outlet conduits 15, 15' to deviate the gas jet stream 18 emitting from the nozzle 16 to a selected one of the conduits 15 or 15'. To obtain multi-dimensional perturbations of an object, two or more actuator devices may be connected to the object to be perturbed.

The valve section of the gas jet actuator device is defined by the portion of the device within the circle 19. The orifice 20 of the nozzle 16, as well as the cross-section of the outlet sections 15, 15' within the circle 19, and the boundary wall section 21 are all of rectangular cross-section. The connecting section 22 of the inlet tube may be of any other cross-section, such as circular. As also shown in FIG. 1, the outlet portion of the outlet sections 15, 15', herein portions 23, are bent at right angles to the inlet section 12 so as to create opposing forces when air pressure is switched from one or the other of the outlet sections 15 and 15'. These outlet sections 23 may also have a different cross-sectional configuration.

The switching means 17, as previously described, is located in the boundary wall section 21 of the conduit. The switching means is comprised of two or more holes 24 provided in the wall section 21 and aligned with a respective one of the outlet conduits 15 and 15'. The switching means 17 is herein constituted of a gate 25 provided with a pad 26 on a face thereof and in alignment with the holes 24. The gates are pivoted on pivot connections 27 with the pads 26 being urged against the respective one of the holes 24 by the spring biasing force urged by the spring 28. A coil 29 is disposed in alignment with the gate 25 and when energized causes the gate 25 to move toward the core 30 of the coil whereby exposing the hole 24 to the outside atmosphere and thereby breaking the vacuum which is created in the pressure bubble area 31, which will be described later with respect to FIG. 2.

The gas jet theory upon which the actuator device of the present invention operates will now be described with reference to the example illustrated in FIG. 1 wherein a two-dimensional configuration is shown, and in logical step sequence first describing the force versus the mass flow rate, then the guide tubes, then the nozzle, and finally the fluidic valve.

Firstly, concerning the force versus the mass flow rate, it is necessary to first determine the force generated in the steady state given the inlet and exit pressures and areas. This is done simply by momentum conservation, the ideal gas equation, and a continuity equation.

More simply, consider the airjet with fixed point support (FIG. 1). A control volume is constructed around the gas jet and is closed at the inlet and two exits. The net force F acting on the gas jet by its supporting structure must be equal to the time rate of change of momentum of the contents of the control volume. If the flow is steady, this balance may be expressed as:

$$F=(\dot{m}_1 u_1 - \dot{m}_2 u_2)i + \dot{m}_i u_i j \tag{4}$$

where subscript i stands for the inlet port, subscripts 1 and 2 stand for the two exit ports, $\dot{m}_j$ is the mass flow rate and $u_j$ is the flow velocity for port j={i,1,2}, and i,j are the x,y unit vectors. The mass flow rates can be further written as:

$$\dot{m}_j = \rho_j A_j u_j \tag{5}$$

where $A_j$ is the area and $\rho_j$ is the local flow density of port j={i,1,2}. In the present design, $A_1=A_2 \approx A_i$.

At the gas jet exits, the static pressures $P_1, P_2$ and temperatures $T_1, T_2$ are assumed to equal atmospheric pressure $P_o$ and temperature $T_o$ where subscript 0 stands for ambient quantities. This is a reasonable assumption because the flow is fully expanded in the guide tubes. The high-pressure air comes to the nozzle inlet through a long flexible nylon tube whose heat conductivity is sufficiently high. It is reasonable to assume that the temperature at the nozzle inlet is close to ambient temperature ($T_1=T_2 \approx T_i=T_o$) The inlet pressure $P_i$ is much higher than the exit pressures ($P_i/P_o \approx 4$–$6$). The ideal gas equation, as applied to the inlet and exits is $$P_j = \rho_j T_j R \tag{6}$$

where j={1 i,0,1,2} and R=287 m$^2$/(s$^{2o}$K) is the gas constant for air. For air at sea level conditions and $T_o$=288° K., $\rho_o$=1.23 kg/m$^3$ and $P_o$=101.3 kPa. From above, $\rho_1 = \rho_2 = \rho_0 < < \rho_i$. Neglecting the small quantity of the flow sucked in through the control openings on the fluidic valve, the continuity equation is $$\dot{m}_i = \dot{m}_1 + \dot{m}_2 \tag{7}$$

In the steady state, either $\dot{m}_1$ or $\dot{m}_2$ is equal to zero, but not both. Assume $\dot{m}_1 \neq 0$ and $\dot{m}_2 = 0$; hence $\dot{m}_i = \dot{m}_1$. From Equation (5)

$$u_i = \frac{\rho_1 A_1}{\rho_i A_i} u_1 \tag{8}$$

Since and $\rho_i > > \rho_1$ and $A_1 \approx A_i$, then $u_i < < u_1$. Hence from Equation (5), $$F \approx \rho_1 A_1 u_1^2 i = \dot{m}_1 u_1 i \tag{9}$$

The outlet sections 32 and 32' of the guide tube turn the flow by 90°. Because the gas jet's force is proportional to the square of the exit flow velocity, the focal point in designing the guide tubes is to minimize any loss from shock waves and turbulence. Unfortunately, sensitivity to operating conditions constrain the design.

The static flow pressures, the temperatures, and the densities at both ends of the guide tubes are the same and equal to the atmospheric values. The gas jet shoots into a guide tube inlet at sonic or supersonic speed. The requirement here is that the jet should not spill over at the inlet; that is to say, the jet should not be split into both guide tubes at the same time.

Theoretically, one may use a diffuser to reduce the jet flow to subsonic, turn the subsonic flow by the desired angle, and finally use a nozzle to accelerate the flow back to supersonic. In this ideal case, the loss is minimized because there is no shock wave formed. Yet this is impractical for two reasons. One is the starting problem. Suppose that a fixed geometry, ideal shock-free diffuser is designed based on the steady jet flow Mach number M. When the jet flow is switched into the diffuser, a shock wave is formed in front of the diffuser. Even though the inlet jet flow reaches M, the shock wave does not go away because the flow behind the shock wave has a lower Mach number and the jet flow will spill over. The other problem is that boundary layer growth prevents diffusion to M=1, because there is a minimum passage area at which the Mach number can be one. For a given Mach number of the jet flow, the Mach number at the point of minimum area (throat) would be very sensitive to the thickness of the boundary layer there. Perturbation in the boundary layer would result in a shock wave, which would be expelled to a position ahead of the diffuser entrance.

Given these difficulties, we use uniform dimension tubing with slightly large cross-section area. If the jet area is much smaller than the tubing area, the flow will not spill over at the guide tube inlet. Such a design also implies that the flow at the guide tube exit must be subsonic and the loss inside the tube is quite large.

The function of the nozzle 16 is to convert the potential energy in pressurized gas into kinetic energy. Since it was mentioned above that supersonic flow does not help much in the gain of thrust, it is enough to design a convergent nozzle to convert high-pressure air into sonic flow. We must now determine the nozzle exit area given the inlet pressure and the required mass flow rate. The design is based on the two-dimensional channel flow theory. Here we only list the main results. Assuming the nozzle is choked, the unit flow rate at the choke point is given by $$\rho_{ne} u_{ne} = \gamma^{\frac{1}{2}} \left( \frac{2}{\gamma+1} \right)^{\frac{\gamma+1}{2(\gamma-1)}} \frac{P_{it}}{(RT_{it})^{\frac{1}{2}}} \qquad (10)$$

where the subscript ne refers to the choke point or nozzle exit, the specific heat ratio $\nu = 1.4$ for air, $T_{it} = T_o$ is the inlet total temperature, and $P_{it}$ is the inlet total pressure. $P_{it}$ can be calculated from Equations (6) and (8):

$$P_{it} = P_i + \frac{1}{2} \rho_i u_i^2 = P_i + \frac{1}{2} \rho_0 \frac{P_0}{P_i} u_1^2 \qquad (11)$$

The nozzle throat area $A_{ne}$ can be calculated from $$\dot{m}_i = A_{ne}(\rho_{ne} U_{ne}) \qquad (12)$$

The fluidic switching valve means 17 is a bistable device that determines the gas jet frequencies. Because it is a fluidic device, its normal operation is sensitive to geometry.

Figure 2:
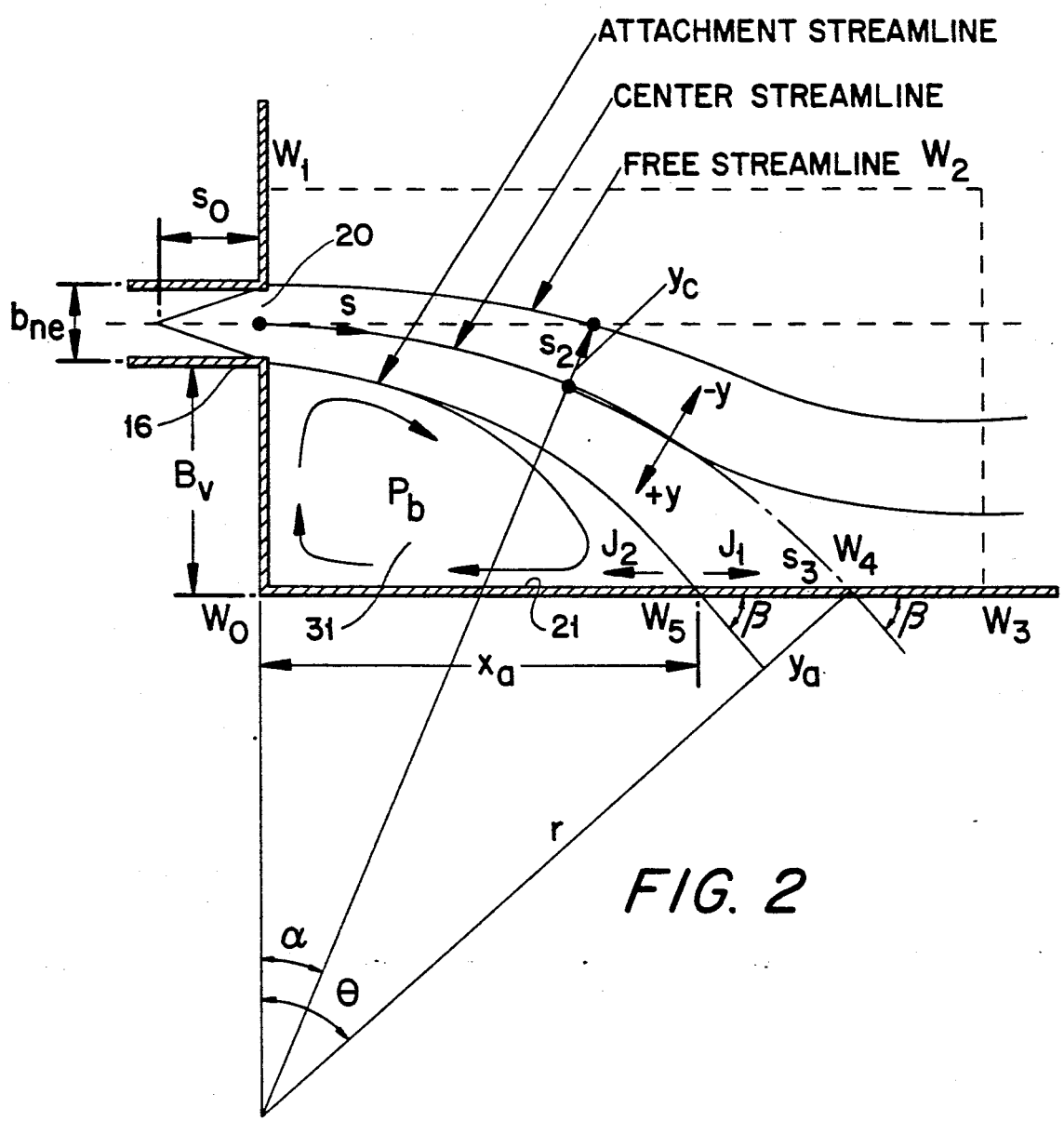
FIG. 2 is an analytical model for jet attachment.

The fluidic valve means 17 operates by the Coanda effect. Consider an incompressible, turbulent, two-dimensional wall jet discharging into a quiescent fluid medium of large extent. Because of viscous interaction between the jet and the surrounding fluid, the jet entrains its surrounding medium. Essentially, the fluid in the medium is set into motion by the discharging jet. Under steady-state conditions, the motion of the jet and the entire surrounding medium becomes established in a particular flow pattern. If the boundary is positioned as shown in FIG. 2, the flow pattern on the side of the jet is significantly changed. The entrainment of fluid into the jet causes a depression between the jet and the boundary wall section 31. The resulting pressure difference across the jet causes it to bend towards the wall 25 and the depression is increased. This process is cumulative and finally the jet attaches to the wall as in FIG. 2. The pressure difference across the bubble balances the force due to the radial acceleration $v^2/r$ where v is the jet velocity and r is the radius of the jet, which in turn is due to the fluid flowing in a curved path. The pressure difference acting on faces $W_o \omega_1$ and $W_o W_3$ of the control column $W_o W_1 W_2 W_3$ causes fluid to be reversed into the jet in order to supply the entrained fluid. The situation is stable because a smaller radius of curvature could require a lower bubble pressure to balance the increased acceleration, but this would draw in more fluid than required for entrainment so the bubble would grow back to its original curvature. The converse is true if the radius of curvature increases from equilibrium.

A splitter or the angulated outlet sections 15 and 15' divides the jet into two directions. As shown in FIG. 1, the control opening 24 is blocked and control opening 24' is open. The jet flow attaches to the right wall according to the Coanda effect, as the splitter and the right wall form a duct to guide the flow to the outlet 23'. If control opening 24' is closed and 24 is opened, the flow switches to the left. The switching must be stable at high frequencies and the flow should not spill over at the splitter intersection 31.

An approximate model for the fluidic valve is given in Appendix A. In this appendix, it is assumed that the basic dimensions of the valve are given, namely the nozzle width $b_{ne}$ and the distance between the nozzle and attachment wall $B_y$. Expressions are found for the location of the attachment point $a_3$, the crossover point of the free streamline with respect to the nozzle axis, and the average pressure in the side bubble 31. Information from this appendix is used to help set design parameters.

To follow the two dimensional calculations above and in Appendix A, the cross-section of the valve and the nozzle are rectangular to prevent secondary flow (the flow in the plane perpendicular to the flow direction) induced by the pressure gradient across the jet.

We constructed the switching valve and nozzle from square cross-section brass tubing, which has high strength and can be made thin-walled to reduce weight. The switching valve contains three tubes of equal cross-section, assembled by soldering. The splitter is formed from two tubes machined with the same angle at their ends. The control openings are made on the third piece. The guide tube is constructed from round cross-section copper tubing, which can be bent easily; it was attached to the valve by soldering. The whole assembly can also be fabricated in plastic by using, for example, stereolithography apparatus.

The nozzle is made by pinching two sides of a tube in a precise mold. A standard connector can be soldered on the other end for the flexible tubing which goes to the air supply. The brass tube for the nozzle has a dimension one size down from the switching valve to allow sliding inside the valve for minor adjustments in the distance $l_s$ to offset modeling error.

The first requirement is that the gas jet should achieve a specified force level, namely 4N (Newtons). Based on Equation (9), the force level can be raised by increasing the exit velocity, the exit area, or both. The exit velocity is limited by the speed of sound. In practice, a further limit is imposed by spillover and a requirement that the jet cross-section is much smaller than that of the guide tube. Hence, increasing the exit area is the main option.

To determine the maximum attainable exit velocity and the exit area required to achieve a 4N force, we constructed a preliminary version of the gas jet to perform experiments. The guide tubes had a diameter of 7mm. the inlet pressure was increased until the jet spilled over, at about 220 kPa (40 psi), at which the force was measured as 2N. The flow velocity at the guide tube exit was estimated by placing a plate attached to a force sensor in front of the exit. From the measured force and Equation (9), we estimated $u_1=200$ m/s.

The flow velocity is primarily determined by the geometry of the chamber and by the inlet pressure at which the jet spills over. Scaling the gas jet dimensions is not expected to significantly change the flow velocity. From Equation (9) with F=4N and $u_1=200$ m/s, the desired guide tube area can be estimated as $A_1=8\times10^{-5}m^2$. From Equation (5), the mass flow rate $m_1=0.02$ kg/s. The valve exit up to the guide tube is made from square-section tubing. From the desired $A_1$, we find that $b_{ve}=h_{nz}=9$mm.

The nozzle throat area $A_{ne}$ can be found from Equations (10)–(12), but first $P_i$ must be determined. It is desirable that $P_i/P_o \approx 4-6$; and we therefore set this ratio at 5, or $P_i=550$ kPa. From the value of $u_1$ above, we calculate from Equation (11) that $P_{it}-P_i=4.6$ kPa, and hence $P_{it} \approx P_i$.

The nozzle throat area can then be calculated as $A_{ne}=1.5\times10^{-5}m^2$. We also selected $A_i=A_1=A_2$ and constructed the nozzle from square cross-section tubing with $h_{nz}=9$mm. The nozzle width $b_{ne}$ can then be found as $b_{ne}=A_{ne}/h_{nz}=1.7$mm.

The remaining dimensions to be determined are the distance $B_v$ between the nozzle orifice 20 and the wall section 31, the splitter angle $v$, the distance $l_s$ between the nozzle exit and the splitter, and the control opening $b_{vc}$ (see FIG. 3) Dimensions $B_v$, $v$, and $l_s$ are related. From FIGS. 1-2, it is seen that the free streamline must be bent passing through the line connecting the nozzle and the splitter to avoid spillover. $B_v$ must be larger than the jet dimension at $s=l_s$, but should not be too large in order to have a high frequency response. The larger is $l_s$, the smaller can be $v$. A smaller $v$ is desirable because a larger $v$ requires a larger acceleration to swing the jet, and the switching frequency would be lower. In other words, increasing $v$ increases the memory and slows down the switching speed. We chose $v=20°$.

For reasons of simplicity of fabrication, the same square tubing was selected for the three parts of the switching valve section 19. The value of $B_v$ is then predetermined at 3.6mm, since the square tubing side is 9mm and the nozzle width is 1.7mm.

To determine $l_s$, we use the analytical model in Appendix A to find the crossing point and the jet attachment point (here they are 5.7mm and 9.1mm). Using Equation (14), for $l_s$ increasing from 20 to 40mm, it is found that the jet doubles its dimension. In general, the splitter should be 3 to 6 times the crossing point.

The control opening $b_{vc}$ should be as large as possible, but is limited by the control device's force. The maximum force required to overcome the low-pressure bubble is theoretically given by Equation (29). Experimentally, it was found that a reasonable value is $b_{vc}=3$mm. The numerical values of the gas jet parameters are summarized in Table 1.

TABLE 1

| Gas Jet Parameters | |
|---|---|
| $b_{ne}$ | 1.7 mm |
| $b_{ve}$ | 9 mm |
| $b_{vc}$ | 3 mm |
| $B_v$ | 3.6 mm |
| $l_s$ | 30 mm |
| $\gamma$ | 20° |
| $h_{nz}$ | 9 mm |

Figure 4:
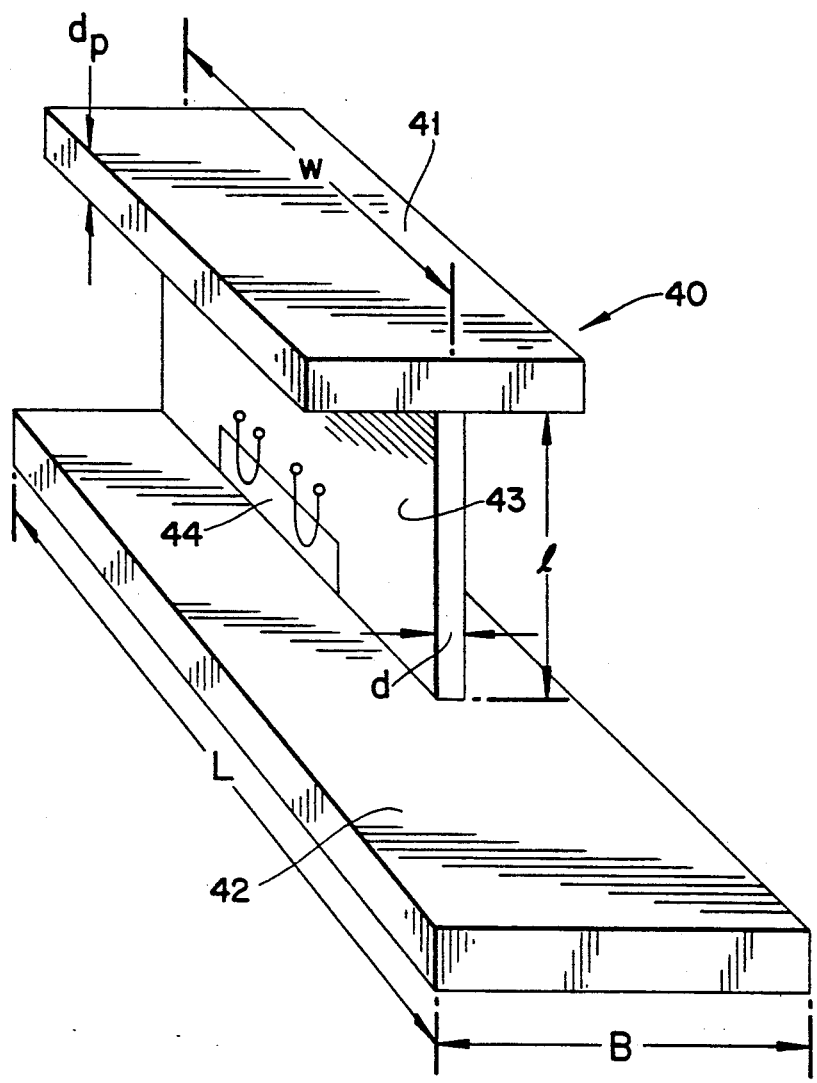
FIG. 4 is a perspective view of a force sensor platform for the gas jet actuator device.

Referring now to FIG. 4 a beam type of force sensor 40, with two platforms 41 and 42 at the end of a beam 43 and two pairs of strain gages 44 at each side forming a bridge supports the gas jet actuator device (not shown). The key dimensions are the beam length l, width w, and thickness $d_p$ and these are based on the dynamics of the sensor, the cuff (described later), and the actuator.

Figure 5:
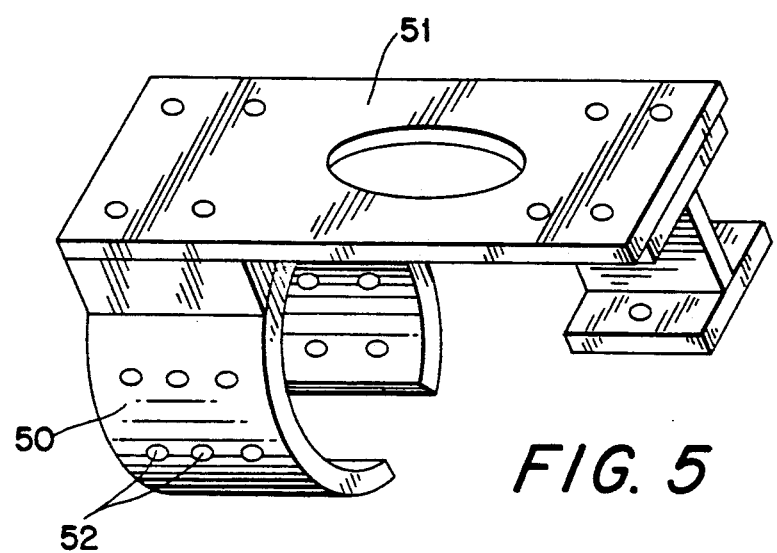
FIG. 5 is a perspective view of a cuff design for attachment to a wrist of an arm to mount the gas jet actuator device.

The beam length l is mainly based on the cuff 50, as shown in FIG. 5. If there is a rotation torque on the cuff 50 along the forearm (not shown), it is very difficult to eliminate a radial rotational skin motion relative to the bone of the human arm. In order to prevent this skin motion, the force has to intersect the axis of the forearm. To do so, a rigid bar 51 is used to connect the cuff 50 and the sensor 40. The length therefore is determined by the wrist thickness ($\approx 20$mm). The beam width w is not as crucial as its thickness because it has less influence on the bending moment inertia. In order to give the gas jet actuator device good support and eliminate vibration in the non-force directions, we set w=2l. The platforms 41 and 42 at the ends of the sensor 40 are for mounting. Their thickness $d_p$ should be at least twice the thickness of the beam d. The other dimensions are designed based on the fit of the gas jet actuator device.

It would be desirable for the beam to be as thin as possible to yield a large strain, but the thinness is limited by the strain gage's maximum strain $\epsilon_{max}$ and the force transmissibility in the frequency range of interest. The maximum strain in the beam from its dimension is given by the expression:

TABLE 2

| Sensor parameters | | |
|---|---|---|
| $\epsilon_{max} = \dfrac{Fld/2}{EI}$ | | (13) |
| d | | 2.54 mm |
| l | | 12.7 mm |

TABLE 2-continued

Sensor parameters $$\epsilon_{max} = \frac{Fld/2}{EI} \quad (13)$$

| | |
|---|---|
| w | 25.4 mm |
| $d_p$ | 4 mm |
| L | 30 mm |
| B | 30 mm | where F is the force, $E=7.056\times10^{10}N/m^2$ is the modulus of elasticity, and I is the area moment of inertia ($d^3w/12$). The material is aluminum. If we set the safety factor of 2 on the maximum strain, then the minimum thickness can be found from Equation (13) as $d_g=1.1mm$.

Force transmissibility requires that the beam is sufficiently stiff so that the natural frequencies are significantly larger (at least 2-3 times) than the frequency range of the system under study, and hence imposes a limit on the minimum thickness. A dynamic model for the force sensor is derived in Appendix B, and an expression for the natural frequencies appears in Equation (40). If we set $w=200$ Hz as the lowest acceptable beam frequency, we find that the minimum thickness due to force transmissibility is $d_f=2.5mm$.

Finally, the beam thickness is given by $d=\max\{d_g,d_f\}=2.5mm$. Thus force transmissibility imposes a more stringent limit than does maximum strain. The sensor parameters are summarized in Table 2. The force sensor was calibrated with a commercial six-axis force sensor (Barry Wright Controls FS6-120A). We tested the frequency response of the force sensor by imparting a force impulse with a sharp tap. It was found that $w=170$ Hz, close to the theoretical value.

As mentioned earlier, the actuator 10 is attached to the wrist of a subject's arm with the cuff 50, as shown in FIG. 5. The subject's wrist is first immobilized with an individually fitted plastic cast made from Aquaplast (Registered Trademark); this cast extends from the hand halfway towards the elbow. Over the plastic cast, the cylindrical aluminum cuff 50 of elliptical cross-section is fastened by means of 12 pressure screws 52, which provide good mechanical attachment without affecting blood circulation.

TABLE 3

Force step response

| | |
|---|---|
| Steady state force | 4N |
| Overshoot | 100% |
| Damping ratio | 0.06 |
| Settling time | 100 ms |
| Rise time | 1 ms |
| Delay to input | 5 ms |

Attached to the cuff bar 51 is an aluminum lever arm which runs distally in front of the hand. The gas jet is attached to the distal end on the side of the hand through the force sensor. The reason for this arrangement is twofold: (1) when the gas jet is aligned with the long axis of the forearm, no torque on the wrist cuff is induced; and (2) the torque on the elbow due to the gas jet is increased with the longer lever arm.

The control system runs on the CONDOR real-time control architecture which is known in the art. The gas jet at the nozzle opening is controlled by two coils 29 with the spring-return gates 25. The analog signals from the strain gages are passed through a signal conditioner device (not shown), which has an instrumental amplifier, a buffer amplifier, and a three-pole Bessel filter for antialiasing with a cutoff frequency of 200 Hz. The conditioned force signal is sampled at 2000 Hz.

The gas jet actuator device 10 has been extensively tested, and meets almost all of the initial specifications. In the test, the device 10 is secured on a rigid table. The air supply is from a 14,000 kPa nitrogen tank regulated down to 550 kPa.

Figure 6:
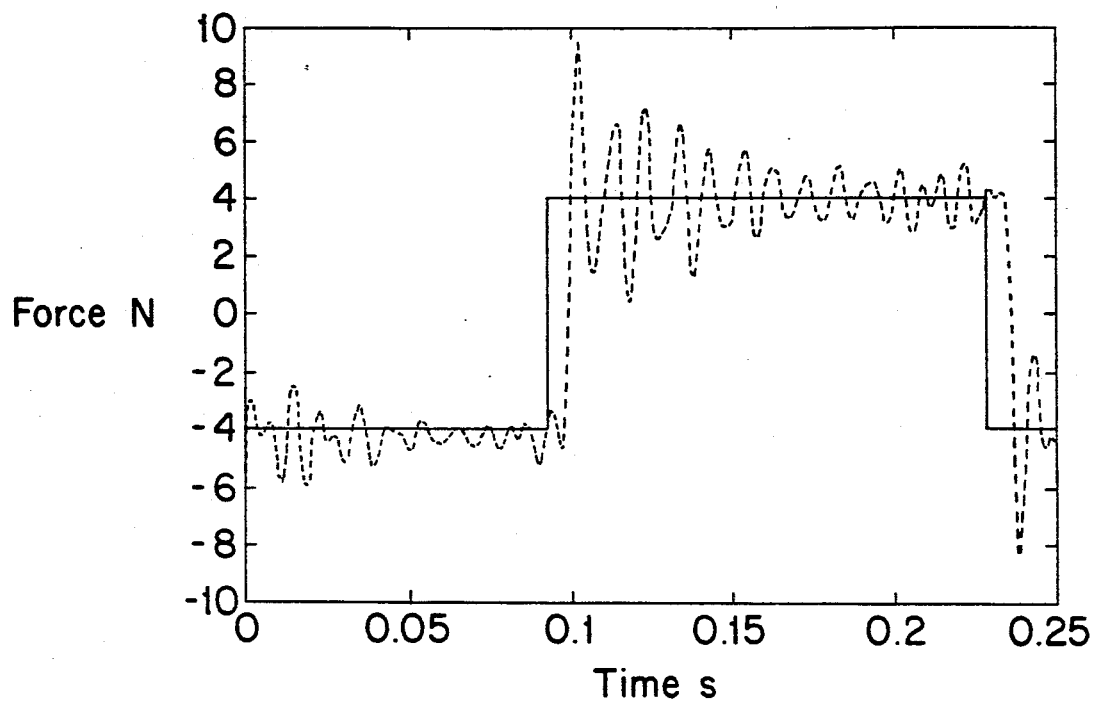
FIG. 6 is a step response illustrating desired force (solid line) versus measured force (dotted line)

FIG. 6 illustrates the step response, whose main features are listed in Table 3. A rise time less than 1 ms shows that the jet stream switching is fast. There is a 5 ms delay to the command issued from the computer, which does not cause a problem for system identification. The coil 29 is responsible for this delay, which limits the upper frequency. The sensor damping ratio is quite low.

Figure 7:
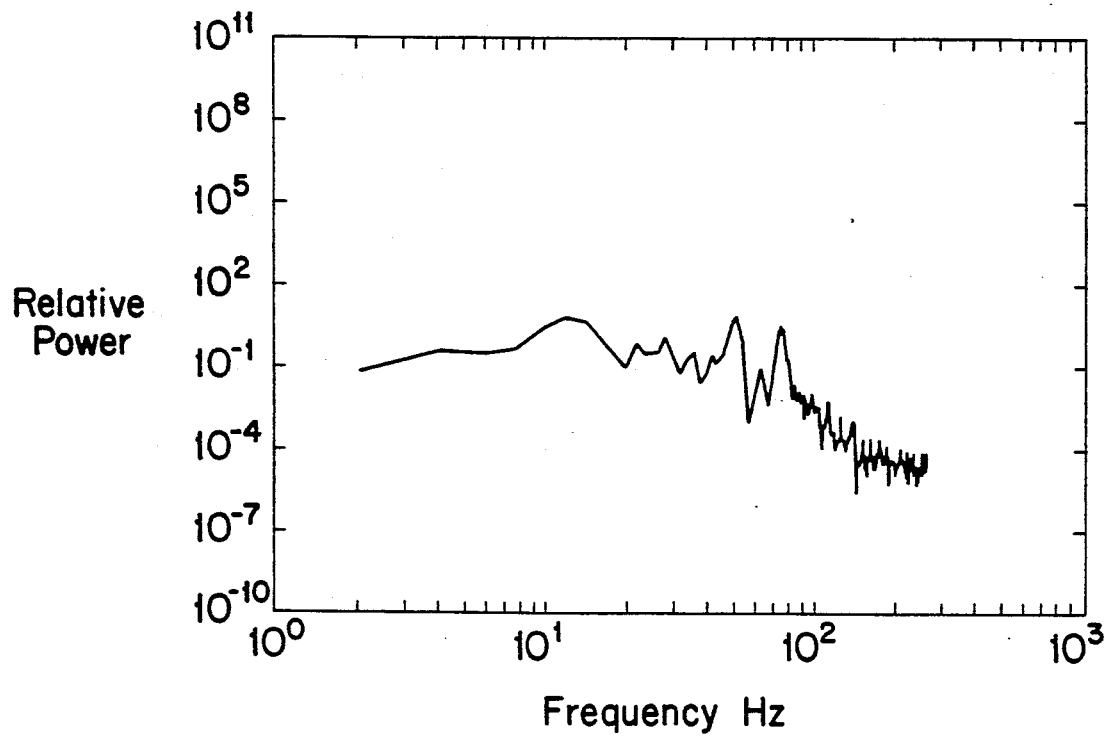
FIG. 7 is a normalized power spectrum of random perturbation.

The power spectrum of the random binary force perturbation is substantially flat to 75 Hz, as shown in FIG. 7, and the usable frequency range extends to about 150 Hz. Hence the gas jet system frequency response exceeds the specifications. Above 75 Hz, the flow tends to go through one side of the gas jet more than the other. Since the step response has shown that the fluid switching is less than 1 ms, the main problem is due to the coil gate device 25, which operates below 100 Hz. Because of the suction force at the control openings 24 and 24' on the gas jet 18, the switching frequency of the coil gate device 25 is further reduced.

The speed of the electromagnetic device can be increased with special step inputs. A large but brief initial current pulse followed by a sustained but much smaller maintenance current step would rapidly lift and hold the gate and expose the control opening 24 to ambient pressure. The coil temperature would not rise excessively since it is proportional to the time integral of the pulse plus step. Moreover, the current required to hold a flapper closed is small because of the suction.

We examined how well the cuff mechanically couples the gas jet to the arm by measuring the cuff's motion. In the test, the subject's elbow, wrist, and hand are fixed to a rigid support. The response of cuff motion to a step in gas jet force was measured in two cuff locations: at the wrist and at the tip of the lever arm.

At the wrist, the cuff movement was between 0.1 and 0.2mm, which is the same as the lowest detectable wrist movement specified previously. This shows that the noise in the wrist movement data due to the compliance of the tissue at the wrist is small. At the tip, the cuff motion was 0.4mm, twice as large as the motion at the wrist. To ascertain whether this motion influences the force transmission from the gas jet to the arm, let us assume that the compliance of tissue and the bonds is approximately linear for small deformations; of course, for large deformations the tissue mechanics are nonlinear.

Figure 8A:
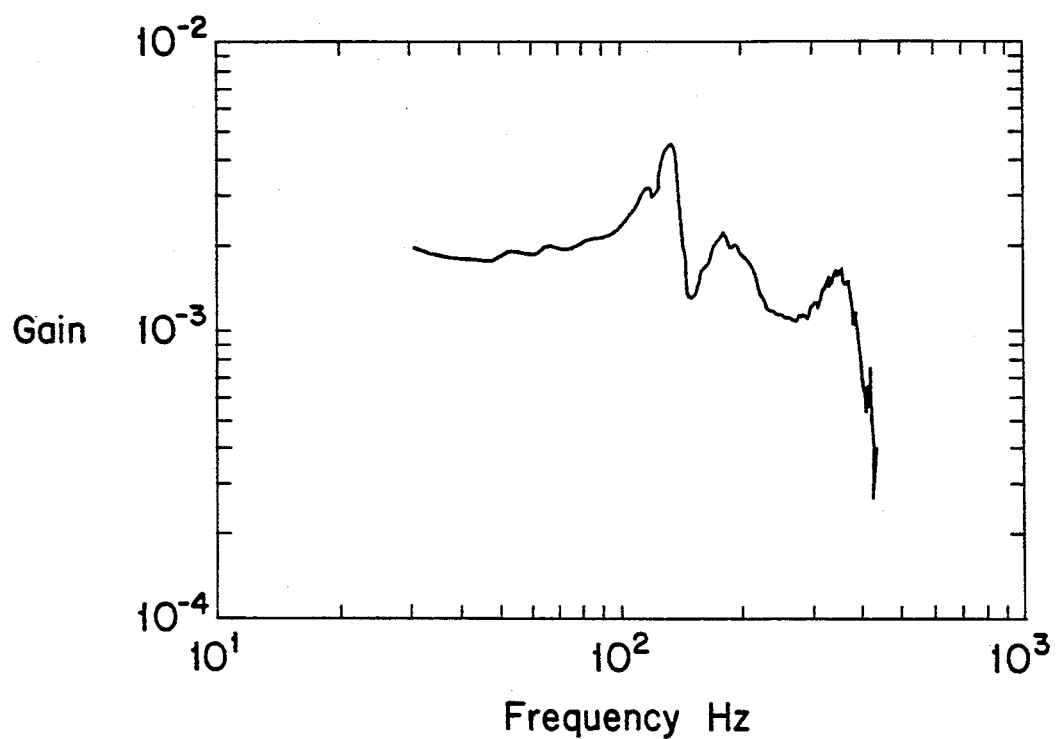
FIG. 8A is a frequency response of the cuff rotation.
Figure 8B:
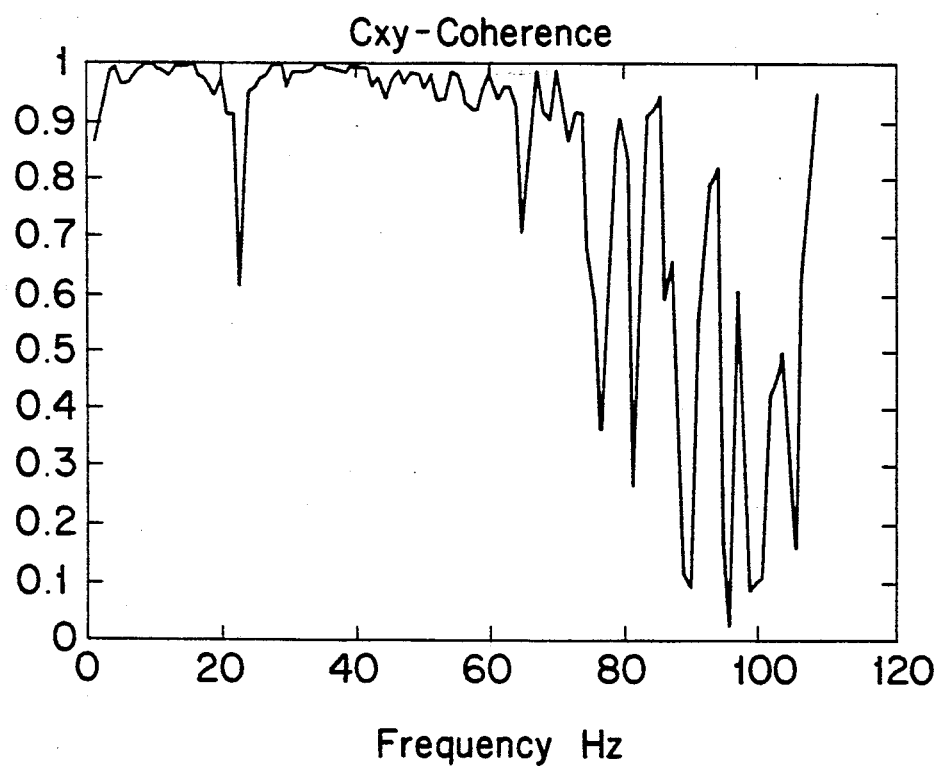
FIG. 8B is a coherence function for cuff rotation.

FIG. 8A is a plot of the frequency response of the transfer function, the ratio of the angular movement of the lever arm about the wrist with forearm fixed and of the force. The frequency response is flat at least to 300 Hz, because the data are filtered with cutoff frequency at 200 Hz for antialiasing. Hence the force transmission is good. The validity of the linear model is demonstrated by the coherence function in FIG. 8B.

APPENDIX A

Using a simplified wall attachment model, we will find the attachment point distance and the streamlines, which are important in designing the gas jet system. The following assumptions are made.

1. The flow is steady, incompressible, and two-dimensional.
2. There is no interaction between the fluid and solid boundaries.
3. The jet velocity is uniform at the nozzle exit.
4. The nozzle width is small compared with the radius of curvature of the jet and the length of the attachment wall.
5. The pressure in the separation bubble is uniform up to the center line, and the center streamline is at ambient pressure.
6. The radius of curvature of the center line of the attached jet is in steady state.
7. The jet flow is independent of the separation bubble pressure.
8. In the bubble the flow entrained by the jet is equal to the returned flow.
9. The control flow is insignificant. The jet is pushed to the wall by the pressure gradient across the jet.

Velocity Profile of a Turbulent-Free Jet. This profile $u$ for an infinitesimal aperture is given by Görtler's equation [18]:

$$u = U_{max} \text{sech}^2 \eta \tag{14}$$

where $U_{max}$ = maximum velocity of jet profile,
  $\eta = \sigma y/s_i$, a non-dimensional jet profile coordinate,
  $\sigma = 12$, the jet spread factor which is an empirical constant,
  $y$ = distance perpendicular to the jet centerline, and
  $s_i$ = distance from the aperture along the jet center line.

The jet momentum flux J per unit length is given by $$J = \rho \int_{-\infty}^{\infty} u^2 dy = \frac{4}{3} \rho U_{max}^2 \frac{s_1}{\sigma} \tag{15}$$

The volume flow Q per unit length is given by $$Q = \int_{-\infty}^{\infty} u\, dy = 2 U_{max} \frac{s_1}{\sigma} = \sqrt{\frac{3 J s_1}{\sigma \rho}} \tag{16}$$

where $U_{max} = \sqrt{3 \sigma J / 4 \rho s_1}$.

Because the nozzle exit is not an infinitesimal aperture, we need to place the origin of the flow a distance $s_o$ upstream of the nozzle, where $s_o$ is chosen such that the volume flow Q out of the nozzle, as given by Equation (16) above with $s_i = s_o$, is the same as the volume flow $Q_s$ of a jet with a uniform profile:

$$Q_s = u_{ne} b_{ne} = \sqrt{\frac{J b_{ne}}{\rho}} \tag{17}$$

where $b_{ne}$ is the nozzle width $u_{ne}$ is the nozzle exit velocity, and $J \cong \rho u_{ne}^2 b_{ne}$ for the uniform jet. Let $s_1 = s + s_o$, where $s_o$ is to be determined. Equations (16) and (17) at $s_1 = s_o$, $$s_o = \sigma b_{ne}/3 \tag{18}$$

Streamlines. The center streamline, the attachment streamline, and the free streamline (the jet free boundary) are shown in FIG. 2. The attachment streamline divides the flow: one portion returns to the bubble and the other proceeds downstream. The center streamline is assumed circular with unknown radius r. Let $Q_y$ be the volume flow contained between the center streamline and y. Since the volume flow cannot cross a streamline, the equation of a streamline is $$Q_y = \int_o^y u\, dy = U_{max} \tanh \eta \tag{19}$$

where Equation (14) was substituted. Let $Q_{ya} = Q_s/2$ be the volume flow between the center line and the attachment streamline, located at $y = y_a$. From Equations (17) and (19), $$\tanh \eta_a = \sqrt{s_o/s_1} \tag{20}$$

where $\eta_a = \sigma y_a/s_1$. At the free streamline, $y = -y_f$ and similarly $$\tanh \eta_f = \tanh \eta_a \tag{21}$$

where $\eta_f = \sigma y_f/s_1$.

The streamline calculation, which is based on an assumed centerline, is valid only before the attachment point. After the attachment point, the centerline assumption and the jet velocity profile (14) are not valid, but this region is unimportant here.

Momentum-Flux Equation. Assume that the momentum flux is conserved in a volume surrounding the attachment point $W_4$, and that the angle of the input momentum flux J is the same as the angle $\beta$ made by the extended centerline [6]. Let $J_1$ be the momentum flux in the direction along the wall and $J_2$ the momentum flux returned to the bubble:

$$J_1 = \rho \int_{-\infty}^{y_a} u_{s3}^2 dy, \quad J_2 = \rho \int_{y_a}^{\infty} u_{s3}^2 dy$$

where $s_3$ is the centerline distance from the aperture to the attachment point $W_4$ and $u_{s3}$ is the velocity profile across the jet there. Then $$J \cos \theta = J_1 - J_2 \tag{22}$$

Substituting Equation (19) and rearranging, $$\cos \theta = \frac{3}{2} \tanh \eta_{s3} - \frac{1}{2} \tanh^3 \eta_{s3} \tag{23}$$

where $\eta_{s3} = \sigma y_a/(s_o + s_3)$.

Geometric Relationships. The six variables to be determined are $s_o$, $s_3$, $r$, $\theta$, $y_a$, and $x_a = \overline{W_0 W_5}$ In addition to the three Equations (18), (19) with s replaced by $s_3$, and (23), the necessary other three equations are derived geometrically (FIG. 2):

$$r\theta = s_3 \tag{24}$$

$$r \sin \theta = x_a + y_a/\sin \theta \tag{25}$$

$$r(1 - \cos \theta) = B_y + b_{ne}/2 \tag{26}$$

Free Streamline Crossing Point. In the design it is necessary to know where the free streamline crosses the nozzle axis. This point $W_f$ corresponds to $s = s_2$, and is found from Equation (21) and the following additional relations:

$$r = (r + y_c) \cos \alpha \tag{27}$$

$$s_c = r\alpha \quad (28)$$

Pressure Inside Bubble. To find this pressure $P_b$, first consider the control volume formed by the centerline and the walls. The pressure forces acting on the control volume are the ambient pressure $P_o$ and the bubble pressure $P_b$; their sum equals the change of momentum. Since $P_b$ and $P_o$ act on the unit depth surface $r - r\cos\theta$, the net pressure force is $r(1-\cos\theta)(P_b - P_o)$. The change in momentum is $(J_1 - J_2) - J$, so that the momentum equation is $$r(1-\cos\theta)(P_b - P_o) = (J_1 - J_2) - J$$

If $\theta = 90°$, then $J_1 = J_2$, and $$P_b = P_o - J/r \quad (29)$$

APPENDIX B

The force sensor can be modeled as a Bernoulli-Buler beam. One end ($x=0$) is clamped and the other end ($x=l$) experiences a vertical force F from the gas jet. The equilibrium equation is [12]

$$(EIw'')'' = 0 \quad (30)$$

where $w(x)$ is the vertical displacement at point x for a horizontal beam. The solution to Equation (30) is the cubic polynomial $$\omega(x) = a_1\left(\frac{x}{l}\right)^2 + a_2\left(\frac{x}{l}\right)^3 \quad (31)$$

where $w(0) = w'(0) = 0$. We identify as generalized coordinates the endpoint displacement $v_1 = w(l) = a_1 + a_2$ and slope $v_2 = w'(l) = (2a_1 + 3a_2)/l$. In terms of the generalized coordinates, Equation (31) becomes $$w(x) = \phi_1(x)v_1 \phi_2(x)v_2 \quad (32)$$

where $\phi_1(x)$ and $\phi_2(x)$ are the shape functions $$\phi_1(x) = 3\left(\frac{x}{l}\right)^2 - 2\left(\frac{x}{l}\right)^3$$

$$\phi_2(x) = -l\left(\frac{x}{l}\right)^2 + l\left(\frac{x}{l}\right)^3$$

Lagrange's equation is $$\frac{d}{dt}\left(\frac{\partial T}{\partial v_i}\right) - \frac{\partial T}{\partial v_i} + \frac{\partial V}{\partial v_i} = q_i \quad i = 1,2 \quad (33)$$

where $q_1 = F$, $q_2 = 0$, and $$V = \frac{1}{2}\int_o^l EI(\omega'')^2 dx \quad (34)$$

$$T = \frac{1}{2}\int_o^l \rho A(\dot{\omega}^2)dx + \frac{1}{2}Mv_1^2 \quad (35)$$

For the kinetic energy, we model the gas jet as a mass $M = 0.175$ kg at the end of the beam. Also, $\rho = 2.7 \times 10^3$ kg/m$^3$ and $A = dw$. Substituting Equations (34) and (35) into (33), we obtain a matrix equation:

$$M\ddot{v} + kv = q \quad (36)$$

where $v = (v_1 v_2), q = F,0)$, and $$m_{ij} = \int_o^l \rho A \phi_i(x)\phi_j(x)dx + M\phi_i(l)\phi_j(l)$$

$$k_{ij} = \int_o^l EI\phi_i''(x)\phi_j''(x)dx$$

Solving, $$M = \frac{\rho Al}{420}\begin{bmatrix} 420M/(\rho Al) + 156 & -22l \\ -22l & 4l^2 \end{bmatrix} \quad (37)$$

$$K = \frac{EI}{l^3}\begin{bmatrix} 12 & -6l \\ -6l & 4l^2 \end{bmatrix} \quad (38)$$

The natural frequencies (36) are obtained by solving the characteristic equation $$|K - \omega^2 M| = 0 \quad (39)$$

The solutions are $$\omega^2 = \frac{EI(2520M \pm 24\sqrt{3}\sqrt{208\rho^2 A^2 l^2 + 1680\rho AlM + 3675M^2}) + 612\rho AlEI}{\rho^2 A^2 l^5 + 12\rho Al^4 M} \quad (40)$$

Although hereinabove extensive discussion is made relative to the use of the gas jet actuator device for the measurement of the mechanical properties of the human arm in a nonconstrained posture, it is also within the ambit of the present invention to utilize the gas jet actuator device on many other objects to measure certain characteristics of the said object when subjected to perturbation by the actuator device. It is pointed out that the construction of the device of the present invention is very lightweight and the only attachment for its operation is a flexible lightweight tube leading to a pressure source. Accordingly, the movement of the object under measure is negligibly affected by the device. Furthermore, the device can be operated over a frequency range which is much greater than known devices of the prior art. It is also conceivable that the switching means to open and block the holes associated with the bubble areas adjacent the nozzle may be constituted by devices other than the coil and gate arrangement as herein described. As also briefly mentioned, the tube 11 may also be constructed of plastics material or other suitable materials not described herein.

I claim:

1. A method of imparting a controllable vibration to a vibratable object, said method comprising:

(i) attaching a gas jet actuator device to said object, said device having conduit means defining an inlet section and a fork section downstream of said inlet section to define diverging outlet sections disposed at predetermined angles, a nozzle in said conduit means upstream of said fork section, and switching means to cause a fluid jet stream from said nozzle to flow in an alternating sequence to said outlet sections by the Coanda effect;

ii) connecting a flexible conduit to said inlet section and to a remote pressure source;

(iii) applying a predetermined gas pressure to said inlet section; and (iv) actuating said switching means to cause said jet stream to alternate between said outlet sections at frequencies within a predetermined frequency range of up to at least 100 Hz to impart controlled vibrations to said vibratable object.

2. A method as claimed in claim 1 wherein said step (iv) comprises actuating said switching means at different frequencies.

3. A method as claimed in claim 2 wherein said step (iii) comprises selecting said predetermined pressure in accordance with specific parameters of said conduit means and nozzle orifice size to generate a desired output force in said diverging outlet sections to impart a known vibration force to said object in a frequency range of up to at least 150 Hz.

4. A method as claimed in claim 1 wherein there is further provided the step of (v) measuring the displacement of said object with position sensing means.

5. A gas jet actuator device for imparting controlled vibrations to an object, said device comprising conduit means defining an inlet section connectible to a source of gas pressure, said conduit means having a fork section downstream of said inlet section to define two diverging outlet sections disposed at predetermined angles, a nozzle in said conduit means upstream of said fork section a predetermined distance therefrom, said fork section being aligned with said nozzle, switching means to cause a pressurized fluid jet stream from said nozzle to be directed to selected ones of said outlet sections by the Coanda effect to impart a controlled vibration force to an object to which said device is attached and in a frequency range of up to at least 100 Hz, said controlled vibration force being predetermined in relationship to the inlet and exit pressures of said guide tube, said orifice of said nozzle, and the inner area of said conduit downstream of said nozzle.

6. A gas jet actuator device as claimed in claim 5 wherein said conduit means is a guide tube having a rectangular cross-section in said fork section, said orifice of said nozzle also having a rectangular cross-section.

7. A gas jet actuator device as claimed in claim 6 wherein said two or more diverging outlet sections are angulated sections defining outlet ports which lie at an angle normal to said jet stream at said nozzle orifice whereby opposed forces are created to cause said vibrations.

8. A gas jet actuator device as claimed in claim 6 wherein a circumferential boundary wall section is defined adjacent said nozzle orifice, said switching means comprising two or more holes in said boundary wall section, each hole being aligned with a respective one of said two or more diverging outlet sections, and controllable hole closing and opening means associated with each outlet to alternately open and close said holes to redirect said pressurized fluid jet stream to selected ones of said outlet sections by breaking a vacuum bubble formed between said pressurized fluid jet stream and its immediate boundary wall section by the opening of said hole associated with said outlet section through which said pressurized fluid jet stream is flowing thereby resulting in a pressure difference across said jet flow to cause said jet flow to bend to redirect same to another outlet section.

9. A gas jet actuator device as claimed in claim 8 wherein said boundary wall section is spaced a predetermined distance from said nozzle orifice and dependent on the distance between said orifice and said fork section and the angular position of said fork sections.

10. A gas jet actuator device as claimed in claim 9 wherein said inlet section is connected to a compressor through a flexible lightweight hose.

11. A gas jet actuator device as claimed in claim 9 wherein said device is secured to an arm attachment bracket securable to a human arm to impart controlled vibrations to said arm when positioned in an unconstrained manner, and sensor means secured to said bracket to detect the responsive movement of said arm.

12. A gas jet actuator device as claimed in claim 9 wherein there are two of said outlet sections disposed in opposition to one another to generate opposing forces to cause an object to which said device is attached to vibrate in a plane, said nozzle orifice having a cross-section much smaller than any one of said outlet sections to prevent spill over of said jet stream.

13. A gas jet actuator device as claimed in claim 8 wherein said hole closing and opening means is comprised of a gate which is spring-biased against a respective one of said holes to block said holes, and means to retract said gate from said hole.

14. A gas jet actuator device as claimed in claim 13 wherein said gate is a spring-biased flap having a sealing head biased against said hole, said means to retract said gate being an electric coil having a low current rating whereby energizing said coil will attract said flap to an open position against its spring tension so that upon deenergization of said coil said flap will automatically return to a closed position.

15. A gas jet actuator device as claimed in claim 5 wherein said frequency range extends to at least 150 Hz.

* * * * *